(12) United States Patent
Périnet et al.

(10) Patent No.: US 9,353,042 B2
(45) Date of Patent: May 31, 2016

(54) PRODUCTION OF ACETATES FROM ACETIC ACID AND ALCOHOLS

(75) Inventors: Alexis Lemieux Périnet, Québec (CA); Jean-Michel Lavoie, Sherbrooke (CA); Esteban Chornet, Sherbrooke (CA)

(73) Assignee: Enerkem, Inc., Montreal, Quebec (CA)

( * ) Notice: Subject to any disclaimer, the term of this patent is extended or adjusted under 35 U.S.C. 154(b) by 6 days.

(21) Appl. No.: 13/135,415

(22) Filed: Jul. 5, 2011

(65) Prior Publication Data
US 2012/0203029 A1    Aug. 9, 2012

Related U.S. Application Data

(60) Provisional application No. 61/401,888, filed on Aug. 20, 2010.

(51) Int. Cl.
*C07C 67/08* (2006.01)

(52) U.S. Cl.
CPC ................................ *C07C 67/08* (2013.01)

(58) Field of Classification Search
CPC ......................................... C07C 67/08
USPC ........................................ 560/265
See application file for complete search history.

(56) References Cited

U.S. PATENT DOCUMENTS

| | | | | |
|---|---|---|---|---|
| 3,024,867 | A * | 3/1962 | Milton | 95/124 |
| 3,096,380 | A * | 7/1963 | Bolen | 585/803 |
| 3,864,103 | A * | 2/1975 | Tuckett et al. | 95/194 |
| 4,435,595 | A | 3/1984 | Agreda et al. | |
| 5,151,547 | A * | 9/1992 | Sato et al. | 560/205 |
| 5,302,747 | A | 4/1994 | Nelson et al. | |
| 6,156,809 | A * | 12/2000 | Clark et al. | 518/719 |
| 6,303,092 | B1 * | 10/2001 | Anand et al. | 423/418.2 |
| 6,693,213 | B1 | 2/2004 | Kolena et al. | |
| 7,160,524 | B2 | 1/2007 | Lederer et al. | |
| 2003/0135069 | A1 * | 7/2003 | Fujita et al. | 560/231 |

FOREIGN PATENT DOCUMENTS

| | | |
|---|---|---|
| CN | 101863760 A | 6/2010 |
| EP | 141975 A | 5/1985 |
| GB | 147337 | 7/1920 |
| WO | 2009105860 A1 | 9/2009 |

OTHER PUBLICATIONS

Waldburger, et al. Membrane Reactors in Chemical Production Process and the Application to the Pervaporation-Assisted Esterification, Chem. Eng. Technol. 19, 117-126, 1996.*
Suwannakarn, et al. A Comparative study of gas phase esterification on solid acid catalysis, Catalysis Letters 114(3-4), 122-128, 2007.*
Kusumaningtyas, "Effect of Zeolite 4A on Water Concentration in the System of the Esterification Reaction of Acetic Acid with 1-butanol," Indo. J. Chem., 2006, 6(2), 132-137.*
Srivastava, "Dealumination of Zeolite Beta Catalyst Under Controlled COnditions for Enhancing its Activity in Acylation and Esterification," Catal. Lett (2009), 130, 655-663.*

* cited by examiner

*Primary Examiner* — Paul A Zucker
*Assistant Examiner* — Mark Luderer
(74) *Attorney, Agent, or Firm* — Raymond J. Lillie

(57) ABSTRACT

A process for producing at least one acetate from acetic acid and at least one alcohol by employing multiple cycles of reacting acetic acid to produce a reaction product including at least one acetate, unreacted acetic acid, unreacted alcohol, and water, followed by drying the reaction product to remove water therefrom. Such process provides for improved yields of acetate.

52 Claims, 3 Drawing Sheets

PRODUCTION OF ACETATES FROM ACETIC ACID AND ALCOHOLS

Figure 1:
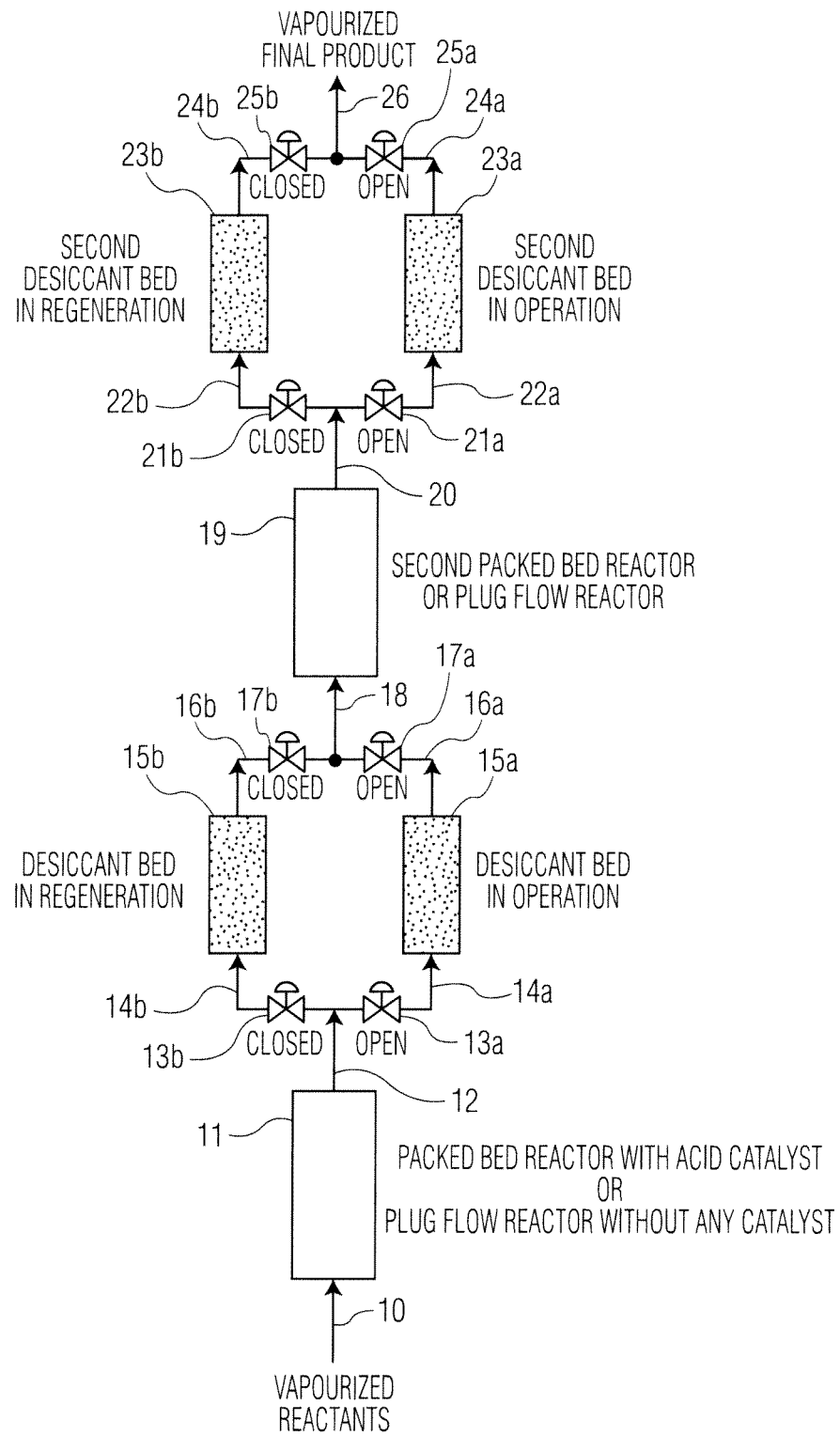

This application claims priority based on provisional application Ser. No. 61/401,888, filed Aug. 20, 2010, the contents of which are incorporated by reference in their entirety.

This invention is directed to the production of acetates (e.g., methyl acetate, ethyl acetate, and butyl acetates) from alcohols (e.g., methanol, ethanol, and butanol). More particularly, this invention is directed to producing acetates from alcohols by employing multiple cycles of reacting acetic acid with at least one alcohol to produce a reaction product including at least one acetate, acetic acid, at least one alcohol, and water, followed by drying the reaction product to remove water therefrom.

Acetates are formed by reacting acetic acid and an alcohol to produce an acetate and water according to the following equation:

$$CH_3COOH + ROH \longleftrightarrow CH_3COOR + H_2O$$

R is an alkyl group, such as, for example, methyl, ethyl, or butyl.

The reaction may be conducted in the presence of a catalyst, or may be conducted without a catalyst.

For example, U.S. Pat. No. 4,435,595 discloses the reaction of methanol with glacial acetic acid (i.e., acetic acid containing less than 0.5% water) in the presence of a catalyst, such as sulfuric acid or a cationic ion exchange resin to produce methyl acetate, through reactive distillation.

Reacting the acetic acid with an alcohol to produce an acetate in the presence of a catalyst is not suitable when the acetate is to be used in particular applications such as the fabrication of pharmaceutical products (e.g., pharmaceutical formulations in which the acetate is employed as a part of a pharmaceutical carrier) or in food additives or flavorings. One can obtain acetates from fermentation processes because acetates are by-products of such processes. The separation of acetates from the remaining fermentation products in downstream purification processes, however, is expensive because of the low concentration of acetates in the final product. Alternatively, one can produce acetates through batch liquid reaction of an alcohol with acetic acid, coupled with distillation and bubbling of an inert gas, such as disclosed in U.S. Pat. No. 5,302,747.

The present invention provides an improved and efficient process for converting acetic acid and at least one alcohol to at least one acetate with a high conversion rate, high selectivity, and provides a product essentially free of water.

In accordance with an aspect of the present invention, there is provided a process for producing at least one acetate from acetic acid and at least one alcohol. The process comprises the following steps:

(a) reacting acetic acid and at least one alcohol to produce a product comprising at least one acetate, acetic acid, at least one alcohol, and water;

(b) drying the product of step (a) to remove water therefrom, thereby providing a product comprising at least one acetate, acetic acid, and at least one alcohol;

(c) reacting the product of step (b) to produce a product comprising at least one acetate, acetic acid, at least one alcohol, and water;

(d) drying the product of step (c) to remove water therefrom, thereby providing a product comprising at least one acetate, acetic acid, and at least one alcohol, wherein the proportion of said at least one acetate present in the product of step (d) is greater than the proportion of said at least one acetate present in the product of step (b); and (e) recovering the at least one acetate from the product of step (d).

The term "remove water therefrom," as used herein, means that all or a portion of the water contained in the reaction products in steps (a) and (c) is removed during each of steps (b) and (d), respectively. In one non-limiting embodiment, a portion of the water in the reaction products of each of steps (a) and (c) is removed during steps (b) and (d), respectively. In another non-limiting embodiment, all of the water in the reaction product of step (a) is removed during step (b), and a portion of the water in the reaction product of step (c) is removed during step (d). In yet another non-limiting embodiment, a portion of the water in the reaction product of step (a) is removed during step (b), and all of the water in the reaction product of step (c) is removed during step (d). In a further non-limiting embodiment, all of the water in the reaction products of each of steps (a) and (c) is removed during steps (b) and (d), respectively.

In a non-limiting embodiment, step (c) (and (d) are repeated at least once. In another non-limiting embodiment, steps (c) and (d) are repeated at least three times, thereby providing at least five cycles of reacting acetic acid with at least one alcohol to produce a product comprising at least one acetate, acetic acid, at least one alcohol, and water, and then drying the product to remove water therefrom. In another non-limiting embodiment, steps (c) and (d) are repeated at least five times, thereby providing at least seven cycles of reacting acetic and with at least one alcohol to produce a product comprising at least one acetate, acetic acid, at least one alcohol, and water, and then drying the product to remove water therefrom. In yet another non-limiting embodiment, steps (c) and (d) are repeated up to nine times, thereby providing up to 11 cycles of reacting acetic acid with at least one alcohol to produce a product comprising at least one acetate, acetic acid, at least one alcohol, and water, and then drying the product to remove water therefrom. With each cycle, the proportion of the at least one acetate increases, thereby increasing the yield of acetate.

In a non-limiting embodiment, the at least one alcohol is one or more of methanol, ethanol, and butanol, and the at least one acetate is one or more of methyl acetate, ethyl acetate, and butyl acetate. In another non-limiting embodiment, the at least one alcohol is methanol, and the at least one acetate is methyl acetate. In another non-limiting embodiment, the at least one alcohol is ethanol, and the at least one acetate is ethyl acetate. In yet another non-limiting embodiment, the at least one alcohol is butanol, and the at least one acetate is butyl acetate.

The reaction steps (a) and (c) may be conducted in the vapor, or gas, phase, or in the liquid phase. Alternatively, at least one of the reaction steps may be conducted wherein liquid acetic acid is reacted with the at least one alcohol in the gaseous state.

In a non-limiting embodiment, at least step (c) of steps (a) and (c) is conducted in the vapor phase. In another non-limiting embodiment, both of steps (a) and (c) are conducted in the vapor phase.

In a non-limiting embodiment when step (c), or steps (a) and (c), is (are) conducted in the vapor phase, such step(s) is (are) conducted at a temperature of from about 118.1° C. (i.e., the boiling point of acetic acid) to about 250°. In another non-limiting embodiment, such step(s) is (are) conducted in the vapor phase at a temperature of from about 130° C. to about 160° C.

In another non-limiting embodiment, when step (c), or steps (a) and (c), is (are) conducted in the vapor phase, such steps is (are) conducted at a pressure of from about 1 atm to about 20 atm. In yet another non-limiting embodiment, such step(s) is (are) conducted at a pressure of from about 1 atm to about 5 atm.

In a further non-limiting embodiment, when step (c), or steps (a) and (c), is (are) conducted in the vapor phase, such step(s) is (are) conducted at a gas hourly space velocity, or GHSV, of from about 100 h$^{-1}$ to about 5,000 h$^{-1}$. In another non-limiting embodiment, such step(s) is (are) conducted at a GHSV of from about 200 h$^{-1}$ to about 2,000 h$^{-1}$.

In yet another non-limiting embodiment, step (c) is conducted in the vapor phase, while step (a) is conducted by reacting acetic acid, which is in the form of a liquid, with at least one alcohol, wherein the at least one alcohol is in the form of a vapor or gas. In general, in such a non-limiting embodiment, step (a) is conducted at a temperature of from about 90° C. to about 250° C.

In a non-limiting embodiment, step (a) is conducted at a molar ratio of acetic acid to the at least one alcohol of from about 0.2 to about 5.0. In another non-limiting embodiment, step (a) is conducted at a molar ratio of acetic acid to the at least one alcohol of from about 0.5 to about 1.5. In yet another non-limiting embodiment, step (a) is conducted at a molar ratio of acetic acid to the at least one alcohol of from about 0.9 to about 1.1. In a further non-limiting embodiment, step (a) is conducted at a molar ratio of acetic acid to the at least one alcohol of about 1:1.

In a non-limiting embodiment, steps (a) and (c) are conducted in the presence of a catalyst. Catalysts which may be employed in steps (a) and (c) include, but are not limited to, alumina, silica-alumina, protonated zeolites, sulfuric acid, phosphoric acid, and protonated ion exchange resins.

In another non-limiting embodiment, the catalyst is a protonated zeolite. Protonated zeolites which may be employed include, but are not limited to, protonated (H+) mordenite, protonated (H+) faujasites, protonated (H+) ZSM-5, protonated (H+) zeolite Beta, and protonated (H+) zeolite Y, or any other large pore zeolite. In one non-limiting embodiment, the protonated zeolite has a Si/Al ratio of from about 10 to about 300. In another non-limiting embodiment, the protonated zeolite has a Si/Al ratio of from about 20 to about 100.

In another non-limiting embodiment, the catalyst is a protonated ion exchange resin. Protonated ion exchange resins which may be employed, include, but are not limited to, protonated macroporous polymer catalysts, and styrene-divinylbenzene copolymers with a sulfonic acid group. An example of such a protonated macroporous polymer catalyst is Amberlyst™70, a product of Rohm and Haas Company, Philadelphia, Pa.

In a non-limiting embodiment steps (b) and (d) are conducted in the presence of a desiccant, which removes all or a portion of the water from the reaction products of each of steps (a) and (c).

Desiccants which may be employed include, but are not limited to, zeolites, activated alumina, silica gel, calcium oxide, magnesium oxide, sodium sulfate, magnesium sulfate, calcium sulfate, magnesium carbonate, potassium carbonate, calcium carbonate, calcium chloride, phosphorus pentoxide, and any salt which can be hydrated, including but not limited to, bicarbonates, including, but not limited to, calcium bicarbonate, bisulfates, and sulfites, including, but not limited to, calcium sulfite.

In one non-limiting embodiment, the desiccant is a zeolite. Zeolites which may be employed include, but are not limited to, molecular sieve zeolites having a pore size from about 3 Angstroms to about 5 Angstroms, such as, for example Linde Type A zeolites 3Å or 4Å; molecular sieve zeolite 13X; and chabazite.

Although the scope of the present invention is not to be limited to any theoretical reasoning, as noted hereinabove, there are instances in which one may not react acetic acid with at least one alcohol in the presence of a catalyst in order to produce at least one acetate. Such instances include, but are not limited to, situations in which the at least one acetate is to be used in the fabrication of pharmaceutical product, or in food additives or flavoring. By conducting multiple cycles of reacting the acetic acid and at least one alcohol, followed by drying the reaction product to remove water therefrom, one is able to provide increased yields of acetate without using expensive downstream purification processes.

When the acetic acid is reacted with at least one alcohol to produce at least one acetate in multiple cycles of reacting the acetic acid with at least one alcohol, followed by drying the reaction product to remove water therefrom, Applicants have discovered that one can obtain increased yields of the at least one acetate without using a significant molar excess of alcohol, than if one cycle of reacting and drying the reaction product were employed.

Furthermore, because water is removed from the reaction product after the acetic acid is reacted with the at least one alcohol, one may use non-glacial acetic acid (i.e., acetic acid containing more than 0.5 wt. % water) as an initial reactant, and be able to obtain high yields of the at least one acetate.

In a non-limiting embodiment, steps (a) and (c) are conducted in the vapor phase, and steps (b) and (d) are conducted in the presence of a desiccant. In another non-limiting embodiment, steps (a) and (c) are conducted in the vapor phase and in the presence of a catalyst, and steps (b) and (d) are conducted in the presence of a desiccant.

In a non-limiting embodiment, acetic acid and at least one alcohol (e.g., methanol, ethanol, or butanol, or a mixture thereof) are vaporized and fed with a carrier gas, such as, for example, nitrogen, to a first reaction vessel. The carrier gas is present in an amount of up to 30 vol. % of the total volume of gas. The at least one alcohol and the acetic acid are reacted in the vapor phase at a temperature of from about 118.1° C. (i.e., the boiling point of acetic acid) to about 250° C., at a GHSV of 100 h$^{-1}$ to 5,000 h$^{-1}$, and at a molar ratio of acetic acid to alcohol of from about 0.2 to about 5.0. The reaction may be conducted in the presence of a catalyst, which may be selected from those hereinabove described. In a non-limiting embodiment, the catalyst may be a protonated zeolite catalyst, or a protonated ion exchange resin catalyst.

The acetic acid and at least one alcohol are reacted in the first reaction vessel to provide a reaction product comprising at least one acetate (e.g., methyl acetate, ethyl acetate, or butyl acetate, or mixtures thereof), at least one unreacted alcohol, unreacted acetic acid, and water. The reaction product then is passed to a first drying vessel or desiccator containing a desiccant as hereinabove described. In a non-limiting embodiment, the desiccant is a molecular sieve zeolite, such as a Linde Type 3Å or 4Å zeolite.

In a non-limiting embodiment, there are provided two desiccators which are operated in parallel. In such an embodiment, the reaction product hereinabove described is passed to one of the desiccators, whereby water is removed from the reaction product, while the other desiccator is "off stream", i.e., the desiccant contained in the "off stream" desiccator is being regenerated. The regeneration of the desiccant, in a non-limiting embodiment, is effected by heating the desiccant to evaporate water absorbed by the desiccant. For example, the desiccant may be heated by contacting the desiccant with a heated gas such as nitrogen. In a non-limiting embodiment, the desiccant is heated to a temperature of up to about 550° C. In another non-limiting embodiment, the desiccant is heated to a temperature of from about 120° C. to about 550° C. Thus, by providing two desiccators in parallel, one may employ one desiccator for drying the reaction product from the reaction vessel, while desiccant is being dried or regenerated in the other desiccator, thereby enabling continuous operation of the process of the present invention.

The reaction product which was passed to the first desiccator is dried, i.e., whereby all or a portion of the water in the reaction product is removed, to provide a product comprising at least one acetate, unreacted at least one alcohol, and unreacted acetic acid. This product then is passed to a second reaction vessel which is operated under the conditions hereinabove described with respect to the first reaction vessel. In the second reaction vessel, the unreacted acetic acid and the unreacted at least one alcohol, are reacted to provide a second reaction product including an additional amount of the at least one acetate, along with lesser amounts of the unreacted at least one alcohol and the unreacted acetic acid, and water.

The second reaction product then is passed to a second desiccator, which contains the same desiccant as the first desiccator. As was the case with the first desiccator, the second desiccator may be in parallel with a corresponding "off stream" desiccator, which contains a desiccant which is being heated to remove absorbed water therefrom, while the second reaction product is being passed through the "on stream" second desiccator, whereby water is removed from the second reaction product. The second reaction product, after drying, comprises at least one acetate, at least one unreacted alcohol, and unreacted acetic acid. The proportion of the at least one acetate in the second reaction product, after drying, is greater than the proportion of the at least one acetate in the first reaction product after drying.

The steps of reacting acetic acid and at least one alcohol to produce a product containing at least one acetate, at least one unreacted alcohol, unreacted acetic acid, and water, in a reaction vessel, followed by drying the reaction product in a desiccator as hereinabove described to remove water from the reaction product may be repeated as many times as desired, depending on the yield and purity of the at least one acetate that one desires to obtain. With each successive cycle of reacting acetic acid and at least one alcohol, followed by drying of the reaction product, the yield of the at least one acetate increases. When one has obtained the desired yield of the at least one acetate, one then recovers the at least one acetate by cooling the reaction product after the last reaction and drying cycle is conducted, and then, if desired, separating the at least one acetate from the remainder of the reaction product.

In an alternative non-limiting embodiment, the at least one alcohol is vaporized and then fed along with a carrier gas such as nitrogen, and in an amount such as hereinabove described, into a first reaction vessel containing a bath of acetic acid in the liquid state. The acetic acid may, in one non-limiting embodiment, be mixed with a catalyst, such as for example, a solid acid catalyst such as a protonated zeolite, or an acid catalyst such as sulfuric acid or phosphoric acid. In such an embodiment, the vaporized alcohol and carrier gas pass through a diffuser in order to fluidize the mixture of the vaporized alcohol and acetic acid, or to obtain enough mixing to ensure mass transfer for the reaction. The excess of acetic acid provides for high conversion of the at least one alcohol to at least one acetate. In a non-limiting embodiment, the reaction of the acetic acid with at least one alcohol is conducted in the first reaction vessel at a temperature of from about 90° C. to about 250° C. (i.e., just below the boiling point of acetic acid). During the reaction, the temperature and pressure are controlled such that entrainment of the acetic acid within the first reaction vessel is moderated, while the reaction product, which includes at least one acetate, at least one unreacted alcohol, some unreacted acetic acid, and water, is passed to a desiccator containing a desiccant, whereby water is removed from the reaction product to provide a product including at least one acetate, at least one unreacted alcohol, and unreacted acetic acid.

The product including the at least one acetate, at least one unreacted alcohol, and unreacted acetic acid then is passed to a second reaction vessel. The unreacted at least one alcohol and acetic acid are reacted in the second reaction vessel in the vapor phase under the vapor phase reaction conditions (i.e., temperature, pressure, GHSV) hereinabove described, and may be reacted in the presence of a catalyst as hereinabove described, thereby increasing the yield of the at least one acetate. This reaction product, which contains at least one acetate, at least one unreacted alcohol, unreacted acetic acid, and water, then is passed to a second desiccator, whereby water is removed to provide a product including at least one acetate, at least one unreacted alcohol, and unreacted acetic acid. The above-mentioned cycle of reacting unreacted acetic acid and at least one alcohol in the vapor phase, followed by drying of the reaction product to remove water therefrom, may be repeated as many times as desired to achieve a desired amount and yield of the at least one acetate.

In yet another non-limiting embodiment, the process of the present invention is carried out in a "batch" mode. In such an embodiment, the at least one alcohol and acetic acid are reacted in a reaction vessel under any of the phases or conditions hereinabove described to provide a reaction product including at least one acetate, at least one unreacted alcohol, unreacted acetic acid, and water. This reaction product is passed to a desiccator to remove water therefrom, and the resulting product, including at least one acetate, at least one unreacted alcohol, and unreacted acetic acid, is recycled to the reaction vessel. Thus, each of the multiple cycles of reacting at least one alcohol with acetic acid, and the drying of the reaction product are carried out in the same reactor and desiccator, respectively, and such cycles are carried out until the desired amount and purity of the at least one acetate are obtained.

In another alternative embodiment, the acetic acid and at least one alcohol are fed to a reaction vessel in which a catalyst and a desiccant are mixed. In such an embodiment, the acetic acid and at least one alcohol are reacted in the reactor in the vapor phase under conditions as hereinabove described to provide a product including at least one acetate, unreacted alcohol, unreacted acetic acid and water. This product is dried immediately by the desiccant contained in the reaction vessel to provide a product including at least one acetate, unreacted alcohol, and unreacted acetic acid.

The dried reaction product, which includes at least one acetate, at least one unreacted alcohol, and unreacted acetic acid then is sent to a second reaction vessel containing a catalyst and desiccant as hereinabove described. In the second reaction vessel, the previously unreacted alcohol and acetic acid are reacted to provide additional acetate, with some remaining unreacted alcohol and acetic acid, and water. This reaction product is dried immediately by the desiccant in the second reaction vessel to provide a product including acetate, unreacted alcohol, and unreacted acetic acid. The amount or proportion of acetic acid present in the product after the second cycle of reacting and drying is greater than that present in the product after the first cycle of reacting and drying. The reacting and drying steps hereinabove described thus may be carried out in a series of reaction vessels, whereby the yield of the at least one acetate increases upon passing the reactants and product through each reaction vessel. Such reacting and drying may be carried out in as many vessels as needed to achieve the desired yield of acetate. In a particular non-limiting embodiment, each of the reaction vessels including a catalyst and desiccant is operated in parallel. Thus, the reactants are passed to one of the reaction vessels, whereby the reactants are reacted, and the reaction products are dried in the reaction vessel, whereby water is removed from the reaction product, while the other reaction vessel is "off stream", i.e., wherein the desiccant in the "off stream" reaction vessel is being regenerated, such as by heating the desiccant to a temperature such as hereinabove described Thus, by providing two reaction vessels in parallel at each stage, one may employ one reaction vessel for reacting the acetic acid and at least one alcohol, and drying the reaction product immediately, while desiccant is being regenerated in the other reaction vessel, thereby enabling continuous operation of the process.

Figure 2:
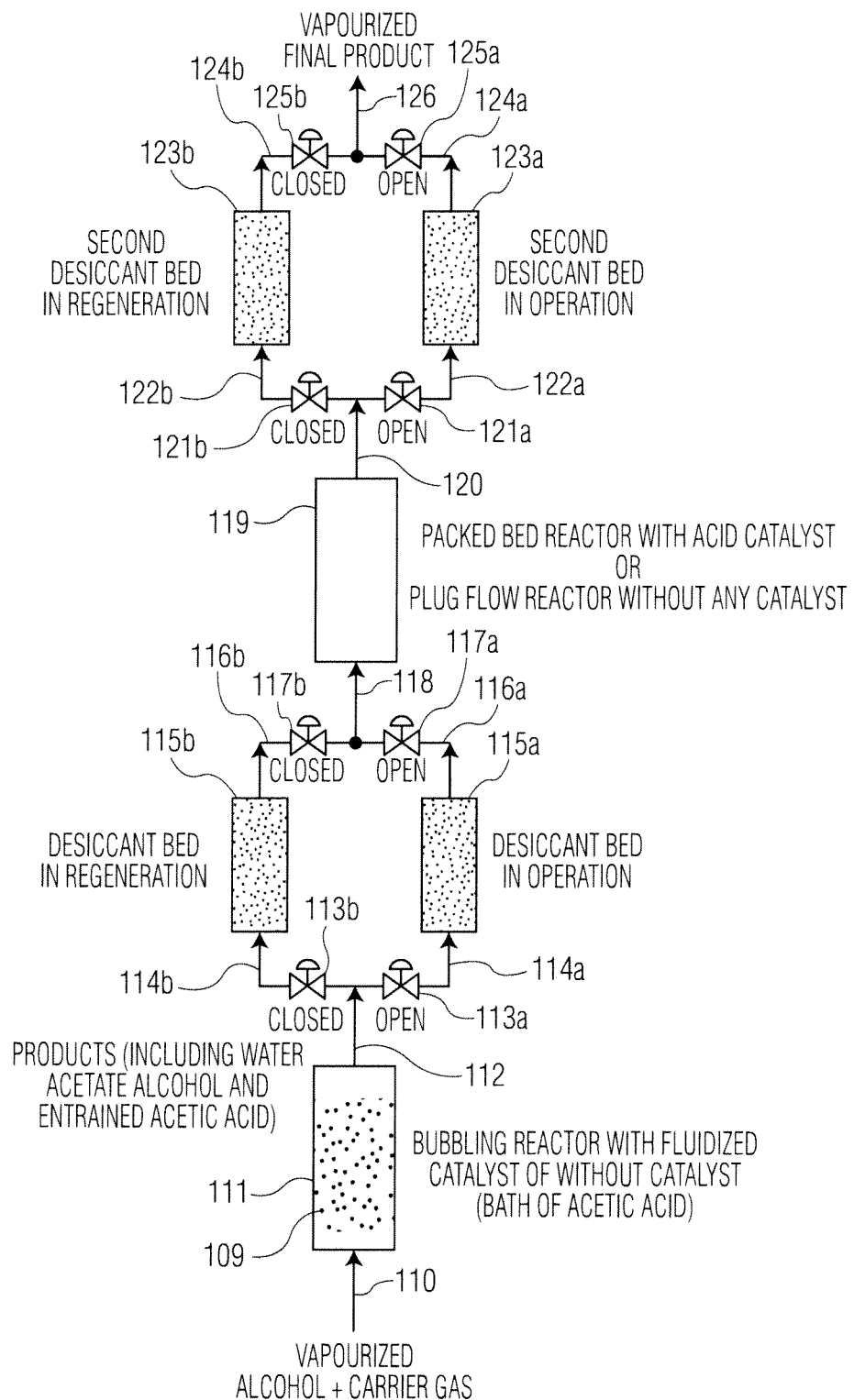
Figure 3:
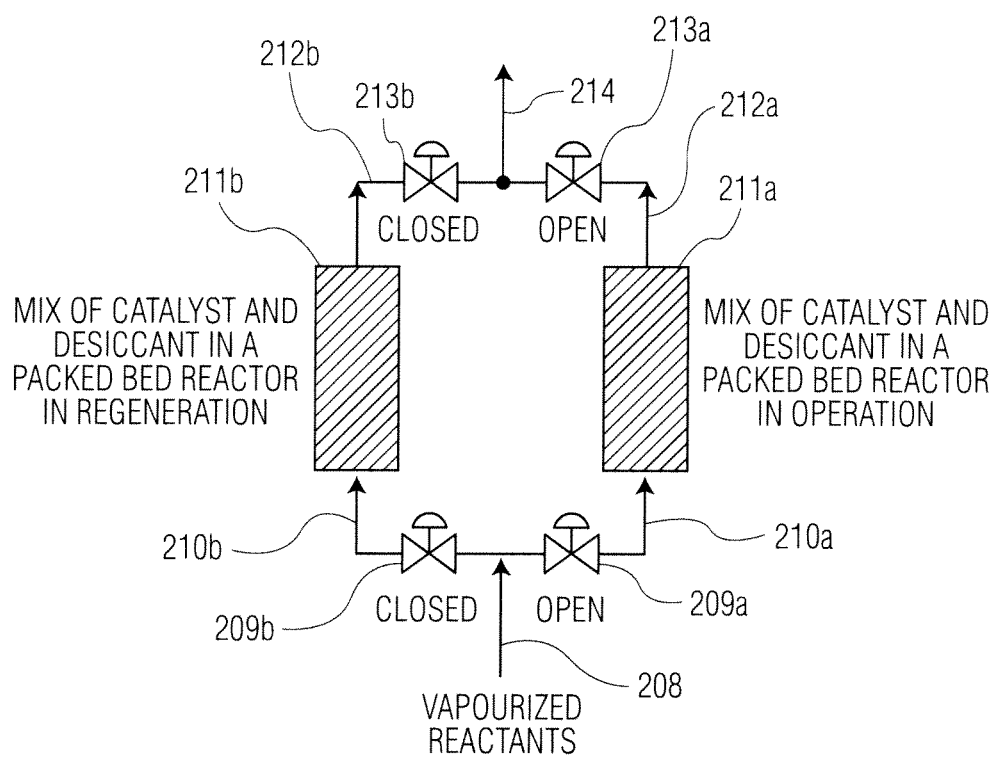

The invention now will be described with respect to the drawings, wherein:

FIG. 1 is a schematic of an embodiment of the present invention in which acetic acid and at least one alcohol are reacted in the vapor phase to produce at least one acetate;

FIG. 2 is a schematic of another embodiment of the present invention in which liquid acetic acid is reacted with at least one vaporized alcohol, in a first reactor, followed by reacting unreacted acetic acid and at least one unreacted alcohol in the vapor phase; and FIG. 3 is a schematic of another embodiment of the present invention in which acetic acid and at least one alcohol are reacted in the vapor phase in a reactor including catalyst and desiccant.

Referring now to the drawings, as shown in FIG. 1, vaporized alcohol, such as methanol, ethanol, and/or butanol, and vaporized acetic acid, along with a carrier gas, such as nitrogen, are passed through line 10 into reactor 11. Reactor 11 may be a packed bed reactor with a catalyst such as those hereinabove described, or may be a plug flow reactor without a catalyst. The acetic acid and the at least one alcohol are reacted in reactor 11 in the vapor phase under conditions hereinabove described, and at a molar ratio of acetic acid to at least one alcohol as hereinabove described. The reaction products which includes at least one acetate, such as methyl acetate, ethyl acetate, and/or butyl acetate, unreacted alcohol, unreacted acetic acid, and water, is withdrawn from reactor 11 through line 12, and passed through open valve 13a and line 14a to desiccator 15a, which contains a desiccant as hereinabove described. In desiccator 15a, water is removed from the reaction product by absorption of water from the reaction product by the desiccant.

Desiccator 15a is operated in parallel with desiccator 15b. While water is being removed from the reaction product in desiccator 15a, desiccator 15b is "off stream", and the desiccant contained in desiccator 15b is being regenerated by heating the desiccant to a temperature such as hereinabove described to remove water therefrom by evaporation. During such time, valves 13b and 17b are closed, and no reaction product passes through lines 14b or 16b. Once the water has been removed from the desiccant in desiccator 15b, valves 13b and 17b are opened, and valves 13a and 17a are closed, whereby the desiccant in desiccator 15a is regenerated by heating the desiccant to remove water therefrom by evaporation. By operating desiccators 15a and 15b is parallel, one is able to provide continuous operation of the process of the present invention without having to shut down the process in order to regenerate the desiccant.

Once water has been removed from the reaction product in desiccator 15a as a result of absorption of the water by the desiccant contained in desiccator 15a, the reaction product, which contains at least one acetate, at least one unreacted alcohol, and unreacted acetic acid, is withdrawn from desiccator 15a through line 16a, passed through open valve 17a, and passed to line 18, and then is fed to reactor 19. Reactor 19, like reactor 11, is a packed bed reactor containing a catalyst as hereinabove described, or a plug flow reactor that does not contain a catalyst. Reactor 19 is operated under the conditions hereinabove described with respect to reactor 11. In reactor 19, the at least one unreacted alcohol and unreacted acetic acid are reacted to provide additional acetate and water. The reaction product, which includes at least one acetate, at least one unreacted alcohol, unreacted acetic acid, and water, is withdrawn from reactor 19 through line 20, and passed through open valve 21a and line 22a to desiccator 23a, which contains a desiccant as hereinabove described. In desiccator 23a, water is removed from the reaction product by absorption of water from the reaction product by the desiccant. While water is removed from the reaction product in desiccator 23a, valves 21b and 25b are closed, whereby no reaction product passes through lines 22b and 24b, and the desiccant in desiccator 23b is regenerated by heating the desiccant in desiccator 23b, thereby evaporating the water absorbed by the desiccant. Once the desiccant in desiccator 23b is regenerated, valves 21b and 25b are opened, and valves 21a and 25a are closed, and the desiccant in desiccator 23a is regenerated.

Once the water is removed from the reaction product in desiccator 23a, the reaction product, which includes at least one acetate, unreacted alcohol, and unreacted acetic acid, is withdrawn from desiccator 23a through line 24a, and passed through open valve 25a to line 26. The reaction product that is withdrawn from desiccator 23a has a higher proportion of the at least one acetate than the reaction product withdrawn from desiccator 15a.

The vaporized reaction product in line 26 then is processed by means known in the art in order to recover the at least one acetate therefrom, such as, for example, by cooling the reaction product, and then separating the at least one acetate from the remainder reaction product.

For example, the vaporized reaction product may be passed through a heat exchanger and/or a condenser in order to cool the product to ambient temperature. The at least one acetate then may be separated from the remainder of the reaction product by means known to those skilled in the art.

Alternatively, if a greater yield or purity of acetate is desired, the reaction product in line 26 may be subjected to one or more additional cycles of reacting and drying as hereinabove described until the desired purity of acetate is obtained.

In another embodiment, as shown in FIG. 2, at least one vaporized alcohol, such as methanol, ethanol, and/or butanol, and a carrier gas, such as nitrogen, are passed through line 110 into reactor 111, which contains a bath of acetic acid in the liquid state. Reactor 111 also may contain a catalyst such as those as those hereinabove described, or may not contain a catalyst. Reactor 111 includes a diffuser 109, through which are passed the vaporized alcohol and carrier gas in order to fluidize the resulting reaction mixture of at least one alcohol and acetic acid, and to provide sufficient mixing to ensure mass transfer of the reaction. In reactor 111, there is a molar excess of acetic acid to provide for high conversion of the at least one alcohol to at least one acetate. Reactor 111 is operated under temperature and pressure conditions that moderate the acetic acid entrainment in reactor 111. In general, reactor 111 is operated at a temperature of from about 90° C. to about 250° C., and at a pressure of from about 1 atm to about 20 atm.

In reactor 111, the at least one alcohol and acetic acid are reacted to provide a reaction product that includes at least one acetate, unreacted acetic acid, unreacted alcohol, and water. The reaction product is withdrawn from reactor 111 through line 112, and passed through open valve 113a and line 114a to desiccator 115a, which contains a desiccant. In desiccator 115a, water is removed from the reaction product through absorption of water from the reaction product by the desiccant.

Desiccator 115a is operated in parallel with desiccator 115b. While water is being removed from the reaction product in desiccator 115a, valves 113b and 117b are opened, and valves 113a and 117a are closed, whereby no reaction product passes through lines 114b and 116b. The desiccant in desiccator 115b is regenerated by heating the desiccant to remove water therefrom by evaporation. Once the desiccant in desiccator 115b is regenerated, valves 113b and 117b are opened, and valves 113a and 117a are closed, and the desiccant in desiccator 115a is regenerated by heating the desiccant.

Once water has been removed from the reaction product in desiccator 115a, the reaction product, which now includes at least one acetate, unreacted alcohol, and unreacted acetic acid, is withdrawn from desiccator 115a through line 116a, and passed through open valve 117a, and then passed through line 118 to reactor 119. The unreacted alcohol and unreacted acetic acid are reacted in reactor 119 in the vapor phase under conditions such as those hereinabove described. Reactor 119 may be a packed bed reactor containing a catalyst, or may be a plug flow reactor which does not contain a catalyst.

In reactor 119, the previously unreacted at least one alcohol and previously unreacted acetic acid are reacted under vapor phase conditions to provide a reaction product including at least one acetate, unreacted alcohol, unreacted acetic acid, and water. The reaction product is withdrawn from reactor 119 through line 120, and then passed through open valve 121a, and line 122a to desiccator 123a, which contains a desiccant. In desiccator 123a, water is removed from the reaction product through absorption of water from the reaction product by the desiccant.

While water is being removed from the reaction product in desiccator 123a, the desiccant in desiccator 123b is being regenerated by heating the desiccant to remove water therefrom by evaporation. While the desiccant in desiccator is being regenerated, valves 121b and 125b are closed, and no reaction product passes through lines 122b and 124b. Once the desiccant in desiccator 123b is regenerated, valves 121b and 125b are opened, and valves 121a and 125a are closed, and the desiccant in desiccator 123a then is regenerated.

After the water is removed from the reaction product in desiccator 123a, the reaction product, which includes at least one acetate, unreacted alcohol, and unreacted acetic acid, is withdrawn from desiccator 123a through line 124a, and passed through open valve 125a to line 126. The reaction product that is withdrawn from desiccator 123a has a higher proportion of the at least one acetate than the reaction product withdrawn from desiccator 115a.

The vaporized reaction product in line 126 then is processed by means known in the art in order to recover the at least one acetate therefrom, such as, for example, by cooling the reaction product, and then separating the at least one acetate from the reaction product. Alternatively, if a greater yield or purity of acetate is desired, the reaction product in line 126 may be subjected to one or more additional cycles of reacting and drying until the desired purity of acetate is obtained. If additional cycles of reacting and drying are employed, such further reacting of unreacted acetate with alcohol, in this embodiment, is conducted in the vapor phase.

In yet another embodiment, shown in. FIG. 3, at least one vaporized alcohol, such as methanol, ethanol, and/or butanol, vaporized acetic acid, and a carrier gas, such as nitrogen, are passed through line 208, open valve 209a, and line 210a to reactor 211a. Reactor 211a contains a catalyst as hereinabove described and a desiccant as hereinabove described.

In reactor 211a, the at least one alcohol and acetic acid are reacted under vapor phase conditions as hereinabove described to provide a reaction product including at least one acetate, unreacted alcohol, unreacted acetic acid, and water. Because the desiccant is admixed with the catalyst, water is removed from the reaction product by the desiccant in reactor 211a immediately upon being formed, thereby providing a reaction product including at least one acetate, unreacted alcohol, and unreacted acetic acid.

While the at least one alcohol and acetic acid are reacted in reactor 211a, followed by the immediate removal of water from the reaction product by the desiccant in reactor 211a, regeneration of the desiccant in parallel rector 211b occurs. Valves 209b and 213b are closed, and no reactants or reaction product passes through lines 210b and 212b, respectively. The desiccant in reactor 211b is regenerated by heating the desiccant as hereinabove described, whereby water is removed from the desiccant by evaporation. Once the desiccant in reactor 211b is regenerated, valves 209b and 213b are opened, and valves 209a and 213a are closed, and the desiccant contained in reactor 211a is regenerated.

After the reacting of the at least one alcohol and acetic acid in reactor 211a followed by the removal of water from the reaction product in reactor 211a are completed, the reaction product, which includes at least one acetate, unreacted alcohol, and unreacted acetic acid, is withdrawn from reactor 211a through line 212a, and passed through open valve 213a to line 214. The reaction product then is subjected to one or more further cycles of reacting the unreacted alcohol and unreacted acetic acid, followed by drying of the reaction product, in one or more reactors containing a catalyst and desiccant as hereinabove described, until a desired yield or purity of the at least one acetate is obtained.

The acetate, after being recovered, in accordance with the present invention, may be used in a variety of applications known to those skilled in the art. For example, the at least one acetate may be used in the fabrication of pharmaceutical products, or in the manufacture of artificial leather, or in food additives or synthetic flavorings, or in perfumes, or as solvents, such as, for example, solvents for resins and oils, solvents for pharmaceutical products, solvents used in food processing, paint solvents, paint thinners, solvents for inks and lacquers, and cleaning solvents for silicon wafers.

Alternatively, the at least one acetate may be used in the synthesis of other desired products, such as alcohols, or anhydrides, such as acetic anhydride. For example, the at least one acetate, such as methyl acetate, ethyl acetate, and/or butyl acetate, may be hydrogenated to produce at least one alcohol, such as methanol, ethanol, and/or butanol.

In one non-limiting embodiment, the process of the present invention may be integrated into a process for producing ethanol from methanol, or a process for producing at least one alcohol, such as ethanol, from synthesis gas. Examples of such processes are described in published U.S. Patent Application No. US2009/0326080. In one non-limiting embodiment, a portion of the carbon monoxide from syngas is reacted with a portion of the hydrogen from such syngas to produce methanol. The methanol then is reacted with a second portion of the carbon monoxide to produce a product which includes methyl acetate (i.e., the "initial methyl acetate") and acetic acid. The acetic acid then is reacted with at least one alcohol to produce at least one alcohol to produce at least one acetate in accordance with the present invention. The "initial methyl acetate" and the at least one acetate produced in accordance with the process of the present invention then are reacted with hydrogen to produce at least one alcohol which includes ethanol.

The invention now will be described with respect to the following examples; it is to be understood, however, the scope of the present invention is not intended to be limited thereby.

EXAMPLE 1

Methanol having a purity of 99.8% and glacial acetic acid, having a purity of 99.7%, were pumped separately through heating vaporizers and then mixed with 10% vol. of $N_2$ in a static mixer. The molar ratio of acetic acid to methanol was 0.5. The methanol, glacial acetic acid, and nitrogen then was passed to a reactor having two zones.

The methanol and glacial acetic acid were reacted at a temperature of 140° C. and a pressure of 1 atm. The first, or reaction, zone of the reactor was filled with Amberlyst 70, a cationic ion exchange resin resistant at temperatures up to 190° C. A bed of zeolite 3Å was in the second, or desiccant, zone.

The gases then were passed through a second reactor having a reaction zone and a desiccant zone as hereinabove described. The gases were passed through the reactor at a GHSV of 500 $h^{-1}$. The final product was condensed at 25° C. and then was cooled further to 4° C. to stop the reaction. Analysis of samples by gas chromatography showed a mass composition of 82.3% methyl acetate, 17.3% methanol, 0.1% acetic acid and 0.3% water. The conversion of acetic acid was 99.4%. After the experiment, the desiccant was regenerated in a muffle furnace at 550° C. for 3 hours. The desiccant showed same efficiency after multiple regeneration cycles.

The resulting products then were hydrogenolyzed in the presence of a catalyst and under conversion conditions that produce methanol and ethanol. The remaining methanol was not affecting significantly the equilibrium of reaction because the conversion of methyl acetate to methanol and ethanol was 92%.

This esterification experiment also was performed under the same conditions but with silicon carbide inert beds instead of desiccant beds of zeolite. The conversion of acetic acid was only 60.6% with a methyl acetate purity of 34.7%.

EXAMPLE 2

Further experiments were performed with glacial acetic acid and anhydrous ethanol as in Example 1, except that the catalyst was changed to H—Y zeolite with a Si/Al ratio of 31, and the molar ratio of acetic acid to ethanol was 1. The reaction temperature was 140° C. and the GHSV was 500 $h^{-1}$. After the glacial acetic acid and anhydrous ethanol were passed through the first reactor, the conversion was 77.2% and the mass composition of the product was 66.7% ethyl acetate, 7% ethanol, 10.7% acetic acid, and 15.6% water. This product then was passed through 2 more catalyst beds alternated with 3 more water removal beds. The conversion of acetic acid was 94% and the ethyl acetate purity was 93%. Up to 8 g of water per 100 g of zeolite 3Å was absorbed.

The disclosures of all patents and publications (including published patent applications) are hereby incorporated by reference to the same extent as if patent and publication were individually incorporated by reference.

It is to be understood, however, that the scope of the present invention is not to be limited to the specific embodiments described above. The invention may be practiced other than particularly described and still be within the scope of the accompanying claims.

What is claimed is:

1. A process for producing at least one acetate from acetic acid and at least one alcohol, comprising:
   (a) reacting acetic acid and at least one alcohol to produce a product comprising at least one acetate, acetic acid, at least one alcohol, and water;
   (b) drying said product of step (a) in the presence of a desiccant to remove water therefrom, thereby providing a product comprising at least one acetate, acetic acid, and at least one alcohol;
   (c) reacting said product of step (b) to produce a product comprising at least one acetate, acetic acid, at least one alcohol, and water;
   (d) drying said product of step (c) in the presence of a desiccant to remove water therefrom, thereby providing a product comprising at least one acetate, acetic acid, and at least one alcohol, wherein the proportion of said at least one acetate present in the product of step (d) is greater than the proportion of at least one acetate present in the product of step (b), wherein steps (c) and (d) are repeated at least five times; and
   (e) recovering at least one acetate from the product of step (d).

2. The process of claim 1 wherein steps (c) and (d) are repeated up to nine times.

3. The process of claim 1 wherein said at least one alcohol is methanol and said at least one acetate is methyl acetate.

4. The process of claim 1 wherein said at least one alcohol is ethanol and said at least one acetate is ethyl acetate.

5. The process of claim 1 wherein said at least one alcohol is butanol and said at least one acetate is butyl acetate.

6. The process of claim 1 wherein at least step (c) of steps (a) and (c) is conducted in the vapor phase.

7. The process of claim 6 wherein steps (a) and (c) are conducted in the vapor phase.

8. The process of claim 1 wherein step (a) is conducted at a molar ratio of acetic acid to the at least one alcohol of from about 0.2 to about 5.0.

9. The process of claim 8 wherein step (a) is conducted at a molar ratio of acetic acid to the at least one alcohol of from about 0.5 to about 1.5.

10. The process of claim 9 wherein step (a) is conducted at a molar ratio of acetic acid to the at least one alcohol of from about 0.9 to about 1.1.

11. The process of claim 1 wherein steps (a) and (c) are conducted in the presence of a catalyst.

12. The process of claim 11 wherein said catalyst is selected from the group consisting of alumina, silica-alumina, protonated zeolites, sulfuric acid, phosphoric acid, and protonated ion exchange resins.

13. The process of claim 12 wherein said catalyst is a protonated zeolite.

14. The process of claim 12 wherein said catalyst is a protonated ion exchange resin.

15. The process of claim 1 wherein said desiccant is selected from the group consisting of zeolites, activated alumina, calcium oxide, magnesium oxide, sodium sulfate, magnesium sulfate, calcium sulfate, magnesium carbonate, potassium carbonate, calcium carbonate, calcium chloride, phosphorus pentoxide, bicarbonates, bisulfates, and sulfites.

16. The process of claim 15 wherein said desiccant is a zeolite having a pore size of from about 3 Angstroms to about 5 Angstroms.

17. The process of claim 6 wherein step (c) is conducted at a temperature of from about 118.1° C. to about 250° C.

18. The process of claim 17 wherein step (c) is conducted at a temperature of from about 130° C. to about 160° C.

19. The process of claim 6 wherein step (c) is conducted at a pressure of from about 1 atm to about 20 atm.

20. The process of claim 19 wherein step (c) is conducted at a pressure of from about 1 atm to about 5 atm.

21. The process of claim 6 wherein step (c) is conducted at a gas hourly space velocity of from about 100 $h^{-1}$ to about 5,000 $h^{-1}$.

22. The process of claim 21 wherein step (c) is conducted at a gas hourly space velocity of from about 200 $h^{-1}$ to about 2,000 $h^{-1}$.

23. The process of claim 7 wherein steps (a) and (c) are conducted at a temperature of from about 118.1° C. to about 250° C.

24. The process of claim 23 wherein steps (a) and (c) are conducted at a temperature of from about 130° C. to about 160° C.

25. The process of claim 7 wherein steps (a) and (c) are conducted at a pressure of from about 1 atm to about 20 atm.

26. The process of claim 25 wherein steps (a) and (c) are conducted at a pressure of from about 1 atm to about 5 atm.

27. The process of claim 7 wherein steps (a) and (c) are conducted at a gas hourly space velocity of from about 100 $h^{-1}$ to about 5,000 $h^{-1}$.

28. The process of claim 27 wherein steps (a) and (c) are conducted at a gas hourly space velocity of from about 200 $h^{-1}$ to about 2,000 $h^{-1}$.

29. The process of claim 6 wherein step (a) is conducted at a temperature of from about 90° C. to about 250° C.

30. A process for producing at least one acetate from acetic acid and at least one alcohol, comprising:
   (a) reacting acetic acid and at least one alcohol in a reaction vessel containing a catalyst and a desiccant, thereby producing in said reaction vessel a first product comprising at least one acetate, acetic acid, at least one alcohol, and water, and whereby said first reaction product is dried by said desiccant in said reaction vessel to provide a second product comprising at least one acetate, acetic acid, and at least one alcohol;
   (b) passing said second product of step (a) comprising at least one acetate, acetic acid, and at least one alcohol to a reaction vessel, containing a catalyst and a desiccant;
   (c) reacting said second product of step (a) in said reaction vessel of step (b) to produce a first product comprising at least one acetate, acetic acid, at least one alcohol, and water, and whereby said first product is dried by said desiccant in said reaction vessel to provide a second product comprising at least one acetate, acetic acid, and at least one alcohol, wherein the proportion of said at least one acetate in the second product of step (c) is greater than the proportion of at least one acetate present in the second product of step (a);
   (d) recovering at least one acetate from the second product of step (c); and
   (e) heating said desiccant of steps (a) and (c) to evaporate water from said desiccant.

31. The process of claim 30 wherein steps (b) and (c) are repeated at least once.

32. The process of claim 30 wherein said at least one alcohol is methanol and said at least one acetate is methyl acetate.

33. The process of claim 30 wherein said at least one alcohol is ethanol and said at least one acetate is ethyl acetate.

34. The process of claim 30 wherein said at least one alcohol is butanol and said at least one acetate is butyl acetate.

35. The process of claim 30 wherein steps (a) and (c) are conducted in the vapor phase.

36. The process of claim 30 wherein said catalyst is selected from the group consisting of alumina, silica-alumina, protonated zeolites, sulfuric acid, phosphoric acid, and protonated ion exchange resins.

37. The process of claim 36 wherein said catalyst is a protonated zeolite.

38. The process of claim 36 wherein said catalyst is a protonated ion exchange resin.

39. The process of claim 30 wherein said desiccant is selected from the group consisting of zeolites, activated alumina, calcium oxide, magnesium oxide, sodium sulfate, magnesium sulfate, calcium sulfate, magnesium carbonate, potassium carbonate, calcium carbonate, calcium chloride, phosphorus pentoxide, bicarbonates, bisulfates, and sulfites.

40. The process of claim 39 wherein said desiccant is a zeolite having a pore size of from about 3 Angstroms to about 5 Angstroms.

41. The process of claim 13 wherein said protonated zeolite has a Si/Al ratio of from about 10 to about 300.

42. The process of claim 41 wherein said protonated zeolite has a Si/Al ratio of from about 20 to about 100.

43. The process of claim 37 wherein said protonated zeolite has a Si/Al ratio of from about 10 to about 300.

44. The process of claim 43 wherein said protonated zeolite has a Si/Al ratio of from about 20 to about 100.

45. The process of claim 1 wherein said acetic acid is non-glacial acetic acid.

46. The process of claim 30 wherein said acetic acid is non-glacial acetic acid.

47. The process of claim 1 wherein, in each of steps (b) and (d), said water is absorbed by said desiccant.

48. The process of claim 30 wherein, in each of steps (a) and (c), said water is absorbed by said desiccant.

49. The process of claim 1, and further comprising:
   (f) heating said desiccant of steps (b) and (d) to evaporate said water from said desiccant.

50. A process for producing at least one acetate comprising methyl acetate from acetic acid and methanol comprising:
   reacting acetic acid and methanol in the vapor phase in the presence of a fixed bed of silicone carbide powder at a gas hourly space velocity of about 500 $h^{-1}$, whereby about 60.6 mass % of said acetic acid is converted to methyl acetate.

51. The process of claim 49 wherein said desiccant is heated to a temperature of up to about 550° C.

52. The process of claim 30 wherein said desiccant is heated to a temperature of up to about 550° C.

* * * * *